United States Patent [19]

Stabile et al.

[11] 4,438,276

[45] Mar. 20, 1984

[54] PROCESS FOR SYNTHESIZING N-ISOPROPYL-N'-O-CARBOMETHOXY-PHENYLSULPHAMIDE

[75] Inventors: Nicolo Stabile, Pavia; Raimondo Motta, Milan; Giancarlo Gosso, Desio, all of Italy

[73] Assignee: Oxon Italia S.p.A., Milan, Italy

[21] Appl. No.: 397,878

[22] Filed: Jul. 13, 1982

[30] Foreign Application Priority Data

Jul. 17, 1981 [IT] Italy ................................ 23001 A/81

[51] Int. Cl.$^3$ ........................................... C07C 143/78
[52] U.S. Cl. ..................................................... 560/13
[58] Field of Search ............................ 560/13; 564/79

[56] References Cited

U.S. PATENT DOCUMENTS 2,829,038  4/1958  Ochsner ................................ 564/79

OTHER PUBLICATIONS

Fieser, "Reagents for Organic Synthesis", pp. 1128–1129, (1967).

*Primary Examiner*—Michael L. Shippen
*Attorney, Agent, or Firm*—Young & Thompson

[57] ABSTRACT

In order to synthesize N-isopropyl-N'-o-carbomethoxyphenylsulphamide, sulphuric chlorohydrin is reacted with a pyridic base between −10° and 50° C., after which anthranilic acid methyl ester is firstly added at 0°–60° C., followed by isopropylamine at 0°–60° C., and finally phosphoric anhydride at 20°–80° C., the product being precipitated by dilution with water and recovered by filtration.

4 Claims, No Drawings

PROCESS FOR SYNTHESIZING N-ISOPROPYL-N'-O-CARBOMETHOXYPHENYL-SULPHAMIDE

BACKGROUND OF THE INVENTION

1. Field of the Invention

This invention relates to an improved original process for synthesising N-isopropyl-N'-o-carbomethoxyphenylsulphamide.

N-isopropyl-N'-o-carbomethoxyphenylsulphamide is known as an intermediate from which an important selective herbicide, namely Bentazon, can be synthesised. This is the reason for the considerable importance of this product and the considerable interest in its production.

2. Description of the Prior Art

It is known from the literature (Kemia-Kemi 9, 1974 page 591) that said intermediate can be prepared by reacting anthranilic acid methyl ester with isopropylsulphamoylchloride, in accordance with the scheme:

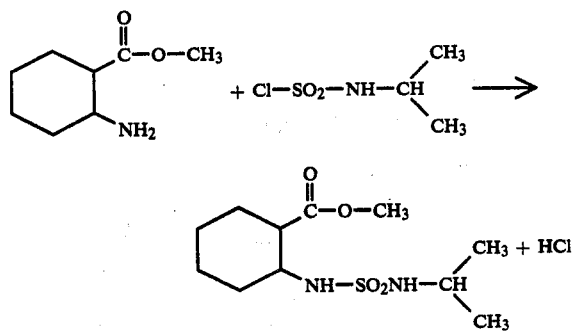

The drawback of this method is that it uses isopropylsulphamoylchloride as raw material, this being an intermediate which is very difficult to synthesise.

In this respect, as described in AGEW. CHEM. INT. ED. ENGL. 20, 151-164 (1981), the following synthesis paths are possible:

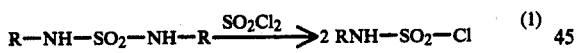

this being a reaction which is difficult to carry out industrially because of the need to use special pressurised equipment;

this being a reaction which uses acetonitrile as solvent, and is recommended only for laboratory tests in that the solvent undergoes partial chlorination to 2,4,6-tris(trichloromethyl)-1,3,5 triazine;

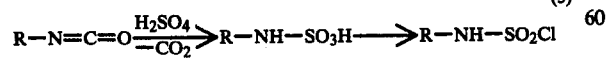

these being reactions involving the use of phosgene, leading to all the dangers connected therewith.

Moreover, when the sulphamoylchloride has been prepared, it must always be purified by distillation under high vacuum in order to prevent decomposition, this requiring the use of special equipment such as film evaporators which complicates and makes costly its industrial application.

SUMMARY OF THE INVENTION

The object of the present invention is to obviate these drawbacks and to provide an improved process for synthesising N-isopropyl-N'-o-carbomethoxyphenylsulphamide which is simple to carry out industrially, does not require separation or purification of intermediate products, and enables the final product to be obtained at high yield and purity.

This process is characterised in that sulphuric chlorohydrin is reacted with a pyridic base, which also acts as the solvent, at a temperature of between $-10°$ C. and $50°$ C. in accordance with the reaction:

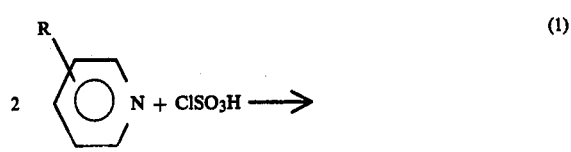

where R is H or $CH_3$;

anthranilic acid methyl ester is added at a temperature of between $0°$ and $60°$ C. in accordance with the reaction:

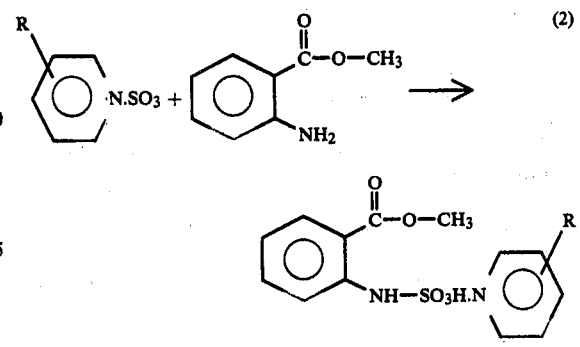

isopropylamine is added at a temperature of between $0°$ and $60°$ C. in accordance with the reaction:

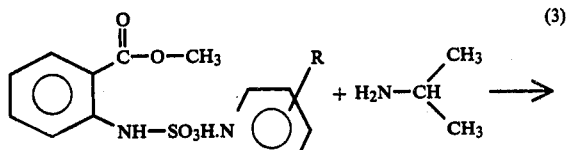

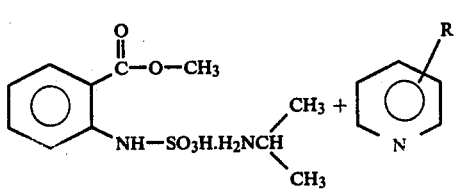

a dehydrating agent is added at a temperature of between 20° and 80° C.; and the product obtained is precipitated by dilution with water and recovered by filtration.

Phosphoric anhydride is preferably used as the dehydrating agent, the fourth reaction of the process then being as follows:

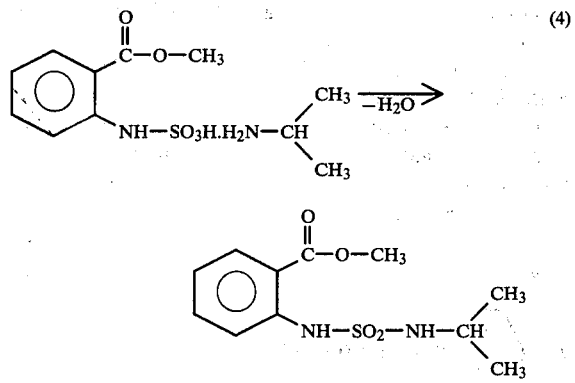

and the pyridic base with which the chlorohydrin is reacted can conveniently be pyridine or α-methylpyridine.

DESCRIPTION OF THE PREFERRED EMBODIMENTS

The invention is illustrated in greater detail hereinafter by way of some practical examples showing how the process according to the invention can be carried out. These examples are purely indicative in character and introduce no limitation.

EXAMPLE 1

141 g of anhydrous α-picoline are fed into a flask, and then 17.5 g of sulphuric chlorohydrin are fed over a period of about half an hour at a temperature of between −10° C. and 0° C.

The mixture is stirred for half an hour, allowing the temperature to rise to +10° C.

15.1 g of methyl anthranilate and then fed over a period of 15 minutes, allowing the temperature to rise to 20°-25° C.

19.3 g of 100% isopropylamine are then fed over a period of 30 minutes, allowing the temperature to rise to 30°-35° C.

The mixture is heated to 50°-55° C. for half an hour.

It is cooled to 20° C. and 49 g of phosphoric anhydride are then fed, after which it is heated to 70°-80° C. for half an hour.

It is cooled, and the mass diluted with 900 ml of $H_2$ at 0° C.

The precipitate is filtered off, washed and dried.

22.5–23 g of N-isopropyl-N'-o-carbomethoxyphenylsulphamide are obtained.

M.P. 106°–108° C.

EXAMPLE 2

158 g of anhydrous pyridine are fed into a flask.

23.3 g of sulphuric chlorohydrin are fed at a temperature of −10° C.-0° C. over a period of 45 minutes.

The mixture is heated to 50° C. over a period of 15 minutes.

15.1 g of methyl anthranilate are fed at 50° C. over a period of about 15 minutes, followed by 27.8 g of 100% isopropylamine at 48° C.-50° C. over a period of 15 minutes.

The mixture is stirred for 15 minutes at 48° C.-50° C.

50 g of phosphoric anhydride are then added, allowing the temperature to rise due to the evolved heat to 70° C.-75° C.

The mixture is stirred at 70° C.-75° C. for 30–60 minutes.

It is cooled and diluted with 1500 ml of water. The precipitate is filtered off, washed and dried.

20.5–21 g of white crystalline N-isopropyl-N'-o-carbomethoxyphenylsulphamide are obtained.

M.P. 107°–108.5° C.

We claim:

1. A process for synthesising N-isopropyl-N'-o-carbomethoxyphenylsulphamide, characterised in that sulphuric chlorohydrin is reacted with a pyridic base, which also acts as the solvent, at a temperature of between −10° C. and 50° C. in accordance with the reaction:

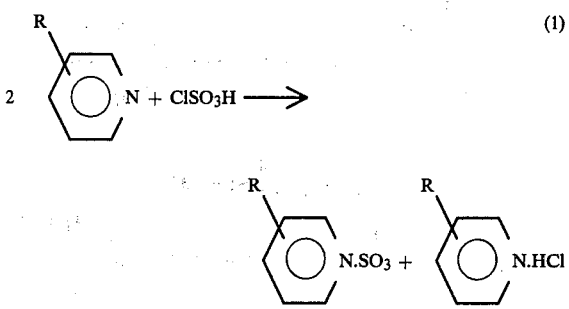

where R is H or $CH_3$;

anthranilic acid methyl ester is added at a temperature of between 0° and 60° C. in accordance with the reaction:

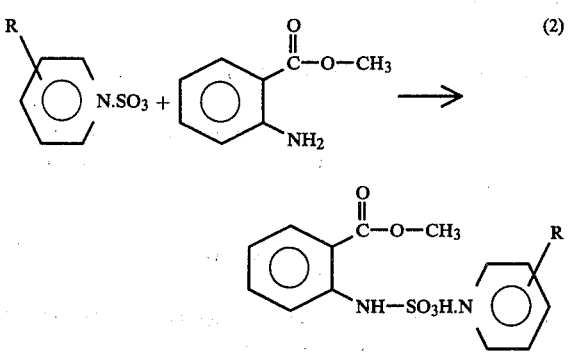

isopropylamine is added at a temperature of between 0° and 60° C. in accordance with the reaction:

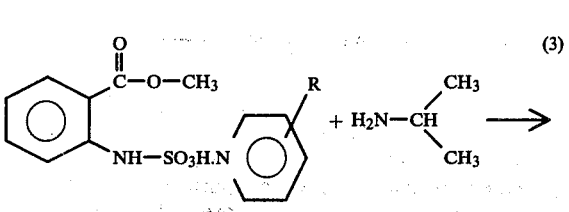

-continued

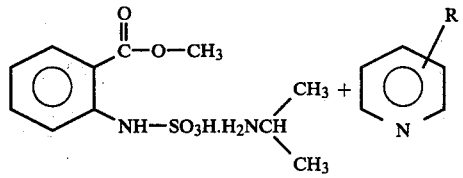 + 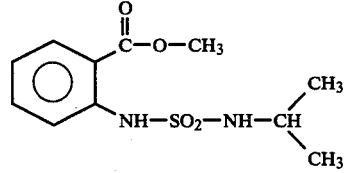

a dehydrating agent is added at a temperature of between 20° and 80° C. in order to effect the reaction:

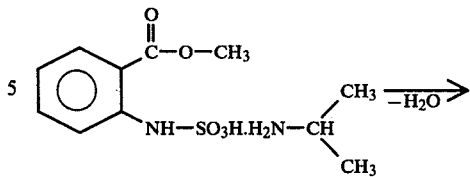

(4)

and the product obtained is precipitated by dilution with water and recovered by filtration.

2. A process as claimed in claim 1, wherein phosphoric anhydride is added as the dehydrating agent.

3. A process as claimed in claim 1, wherein the pyridic base used is pyridine.

4. A process as claimed in claim 1, wherein the pyridic base used is α-methylpyridine.

* * * * *